US007245693B2

(12) United States Patent
Buck et al.

(10) Patent No.: US 7,245,693 B2
(45) Date of Patent: Jul. 17, 2007

(54) X-RAY INSPECTION SYSTEM HAVING ON-AXIS AND OFF-AXIS SENSORS

(75) Inventors: Dean C. Buck, Loveland, CO (US); Tracy Eliasson, Boulder, CO (US); Anthony C. Turner, Drake, CO (US); Ronald K. Kerschner, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 120 days.

(21) Appl. No.: 11/145,073

(22) Filed: Jun. 2, 2005

(65) Prior Publication Data

US 2006/0274883 A1 Dec. 7, 2006

(51) Int. Cl.
*G01N 23/00* (2006.01)
(52) U.S. Cl. ............................. 378/21; 378/58; 378/207
(58) Field of Classification Search ............ 378/21–27, 378/57, 58, 207; 250/358.1–360.1
See application file for complete search history.

(56) References Cited

U.S. PATENT DOCUMENTS 4,516,261 A * 5/1985 Harding et al. ............. 382/131
6,748,046 B2 6/2004 Thayer
6,940,942 B2 * 9/2005 Ullberg ....................... 378/26
7,123,684 B2 * 10/2006 Jing et al. .................... 378/37
2004/0184576 A1 9/2004 Meyer

* cited by examiner

*Primary Examiner*—Jurie Yun

(57) ABSTRACT

An x-ray inspection system. The x-ray inspection system includes an x-ray source, an on-axis x-ray sensor, at least one off-axis x-ray sensor, a fixture, and an accumulation circuit. The on-axis x-ray sensor is configured to capture on-axis images of radiation from the x-ray source. The x-ray source is displaced from the on-axis x-ray sensor, and the x-ray source and the on-axis x-ray sensor are positioned on an axis conceptually drawn between the x-ray source and the on-axis x-ray sensor. At least one off-axis x-ray sensor is configured to capture off-axis images of radiation from the x-ray source, wherein each off-axis x-ray sensor is positioned off the axis. The fixture is configured to maintain an article between the x-ray source and the on-axis and off-axis x-ray sensors, and the accumulation circuit is configured to receive and accumulate images captured by the on-axis and off-axis x-ray sensors.

19 Claims, 10 Drawing Sheets

X-RAY INSPECTION SYSTEM HAVING ON-AXIS AND OFF-AXIS SENSORS

BACKGROUND

Manufacturers of modern electronic devices, circuits, and systems are able to maintain the quality of their products by the use of inspection steps at a number of stages in the fabrication process. The tools used for such inspections include x-ray inspection systems of various types which are typically classified into two major categories, two-dimensional (2-D) systems and the more recent three-dimensional (3-D) inspection systems. Detailed inspections of areas that are either too small to be seen visually with the unaided eye or are obscured from direct view on printed circuit boards and other electronic articles are often made using such systems. Solder joints on printed circuit boards are of particular interest as these connections often have defects, such as voids, that can negatively impact the reliability of such products.

Two-dimensional systems typically have one area detector that captures and produces a single radiographic image referred to as a 2-D image. An object placed between the x-ray source and the x-ray detector or sensor casts a shadow on the detector and thereby produces an image. Such systems have the advantage of being simple, fast, and relatively inexpensive. However, when more than one objects lies within the x-ray beam, as is often the case with double-sided printed circuit boards, objects on one side of a board and objects on the other side of the board can produce overlapped images. As a result, information important to the inspection can be lost.

Three-dimensional systems use various techniques to capture multiple images of an object and produce images of plane sections through the object referred to as 3-D images. Such techniques are generally referred to as laminagraphic or tomographic techniques. Three-dimensional systems can provide resolution to the problem of overlapping objects. Multiple images of a printed circuit board region are captured at different angles. These multiple images are then processed using tomographic techniques to result in a single image with that single image being an image of a plane section through the object space. Thus, the object imaged may be, for example, from the top, the bottom, or within the printed circuit board.

Laminography is based on the correlated motion of an x-ray source, a detector and an object to be inspected. The x-ray source and the detector are typically moved synchronously in circles 180 degrees out of phase. As a result, the location of the projected images of points within the object moves also. Only points from a particular plane, the so called focal plane, will be projected always at the same location onto the detector and therefore imaged sharply. Object structures above and below the focal plane will be projected at different locations. Because of that, they aren't imaged sharply and will be superimposed as a background intensity to the focal plane.

Digital laminography, or tomosynthesis, is based on the correlated position of the x-ray source and x-ray detector. The source and detector are translated in opposite directions and are positioned at discrete locations when the image is captured. This enables the digital storage of a series of discrete projections which can be subsequently combined.

Linear scan laminography and off axis tomosynthesis is based on the correlated position of the object, the x-ray source, and the x-ray detector. The source and detector are stationary relative one to the other, but move relative to the printed circuit board region. A region is captured at different angles at different times and subsequently combined.

SUMMARY

In representative embodiments, an x-ray inspection system is disclosed. The x-ray inspection system comprises an x-ray source, an on-axis x-ray sensor, at least one off-axis x-ray sensor, a fixture, and an accumulation circuit. The on-axis x-ray sensor is configured to capture on-axis images of radiation from the x-ray source. The x-ray source is displaced from the on-axis x-ray sensor, and the x-ray source and the on-axis x-ray sensor are positioned on an axis conceptually drawn between the x-ray source and the on-axis x-ray sensor. At least one off-axis x-ray sensor is configured to capture off-axis images of radiation from the x-ray source, wherein each off-axis x-ray sensor is positioned off the axis. The fixture is configured to maintain an article between the x-ray source and the on-axis and off-axis x-ray sensors, and the accumulation circuit is configured to receive and accumulate images captured by the on-axis and off-axis x-ray sensors.

In another representative embodiment, a method for inspecting an article by the use of x-rays is disclosed. The method comprises providing an x-ray source, an on-axis x-ray sensor, at least one off-axis x-ray sensor, and a fixture, placing the article in the fixture, irradiating the article with radiation emitted from the x-ray source, capturing on-axis image by the on-axis x-ray sensor of a region of the article, capturing off-axis image by each off-axis x-ray sensors of other regions, and accumulating the captured images. The on-axis x-ray sensor is configured to capture on-axis images of radiation from the x-ray source. The x-ray source is displaced from the on-axis x-ray sensor. The x-ray source and the on-axis x-ray sensor are positioned on an axis conceptually drawn between the x-ray source and the on-axis x-ray sensor. Each off-axis x-ray sensor is configured to capture off-axis images of radiation from the x-ray source, and each off-axis x-ray sensor is positioned off the axis. The fixture is configured to maintain an article between the x-ray source and the on-axis and off-axis x-ray sensors.

Other aspects and advantages of the representative embodiments presented herein will become apparent from the following detailed description, taken in conjunction with the accompanying drawings.

BRIEF DESCRIPTION OF THE DRAWINGS

The accompanying drawings provide visual representations which will be used to more fully describe various representative embodiments and can be used by those skilled in the art to better understand them and their inherent advantages. In these drawings, like reference numerals identify corresponding elements.

DETAILED DESCRIPTION

Figure 1:
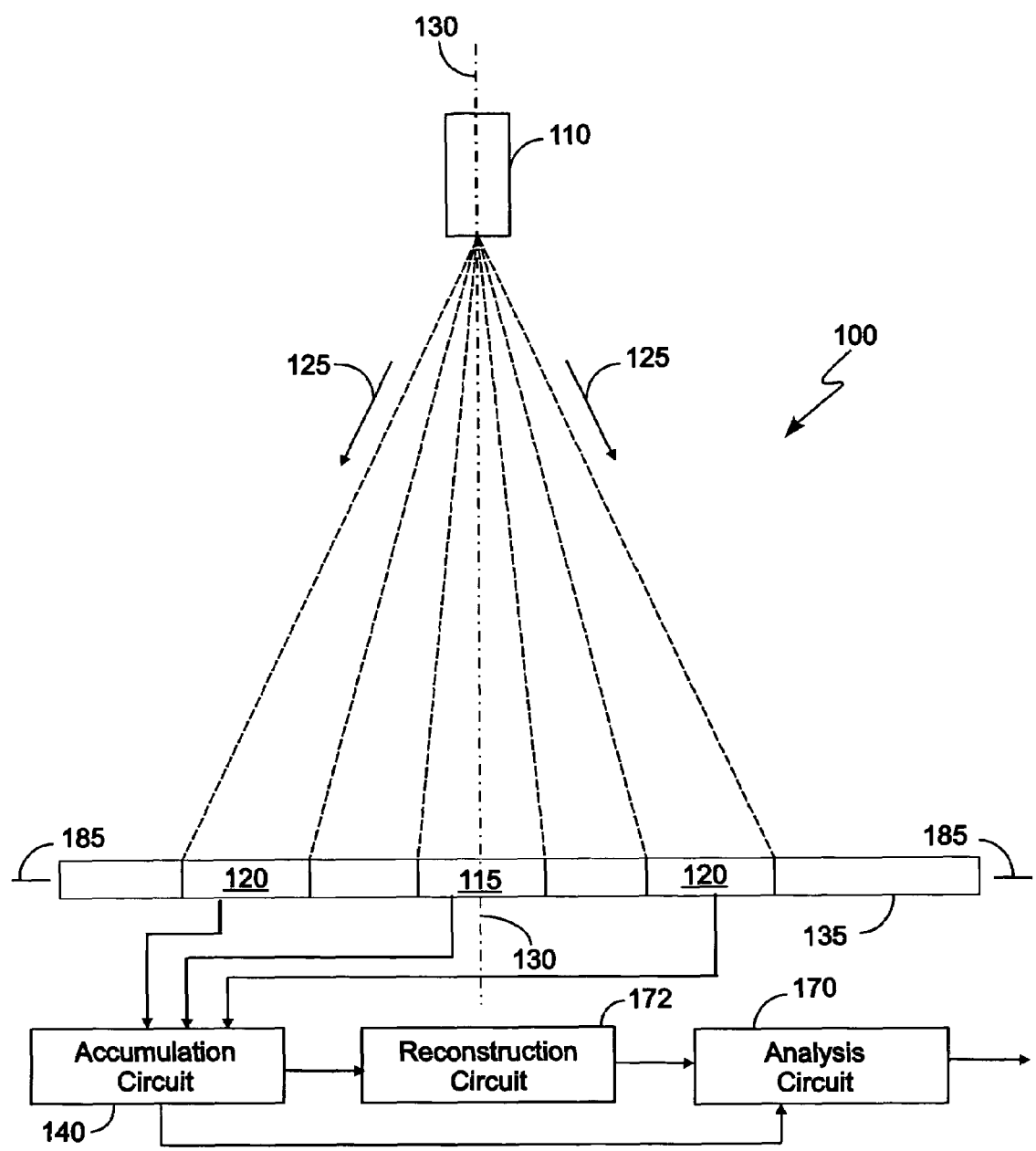
FIG. 1 is a drawing of a block diagram of an x-ray inspection system as described in various representative embodiments.

As shown in the drawings for purposes of illustration, the present patent document discloses novel tomography imaging systems and novel methods for using tomography imaging systems. Previous systems have not used an on-axis sensor with other than on-axis sensors. Transmission x-ray inspection systems employ a single x-ray source and a single x-ray sensor. In operation, the x-ray source is located on one side of an article being inspected and the on-axis sensor being located on the other side. The x-ray source and the x-ray sensor are positioned on an axis that generally is perpendicular to an inspection plane. The transmission system provides a two-dimensional (2-D) image of what is in reality a three-dimensional article.

Advantages of the representative embodiments disclosed herein are enhanced information content from the images obtained and the ability to more accurately calibrate the system with respect to resolution and position.

In the following detailed description and in the several figures of the drawings, like elements are identified with like reference numerals.

FIG. 1 is a drawing of a block diagram of an x-ray inspection system 100 as described in various representative embodiments. In FIG. 1, an x-ray source 110, such as that generated by a simple x-ray tube, is displaced vertically from an on-axis x-ray sensor 115. The on-axis x-ray sensor 115 is sensitive to and configured to capture radiation 125 from the x-ray source 110. The x-ray source 110 and the on-axis x-ray sensor 115 are both positioned on an axis 130 conceptually drawn between the x-ray source 110 and the on-axis x-ray sensor 115 with the surface of the on-axis x-ray sensor 115 in a plane whose normal is parallel to the axis 130. In addition, to the on-axis x-ray sensor 115 one or more off-axis x-ray sensors 120 sensitive to and configured to capture radiation 125 from the x-ray source 110 are positioned at locations off of the axis 130. In representative embodiments, the on-axis x-ray sensor 115 is coplanar in plane 185 with the off-axis x-ray sensor(s) 120. In other representative embodiments, the on-axis x-ray sensor 115 is not coplanar with the off-axis x-ray sensor(s) 120.

In alternative embodiments, the on-axis x-ray sensor 115 and the off-axis x-ray sensors 120 can be logical parts of an area x-ray sensor 135 as shown in FIG. 1 or may be physically separate x-ray sensors 115,120. Regardless, x-ray radiation 125 received by the on-axis x-ray sensor 115 and the off-axis x-ray sensors 120 creates signals within these sensors which produce images that are collected by an accumulation circuit 140. The accumulation circuit 140 is configured to accumulate images produced by the on-axis and off-axis x-ray sensors 115,120. These accumulated images 165 can be transferred to a reconstruction circuit 172 for reconstruction of layer images or transferred to an analysis circuit 170 for analysis as will be explained in the discussion of FIG. 2. The reconstructed images can be transferred from the reconstruction circuit 172 to an analysis circuit 170 as will also be explained in the discussion of FIG. 2.

Figure 2:
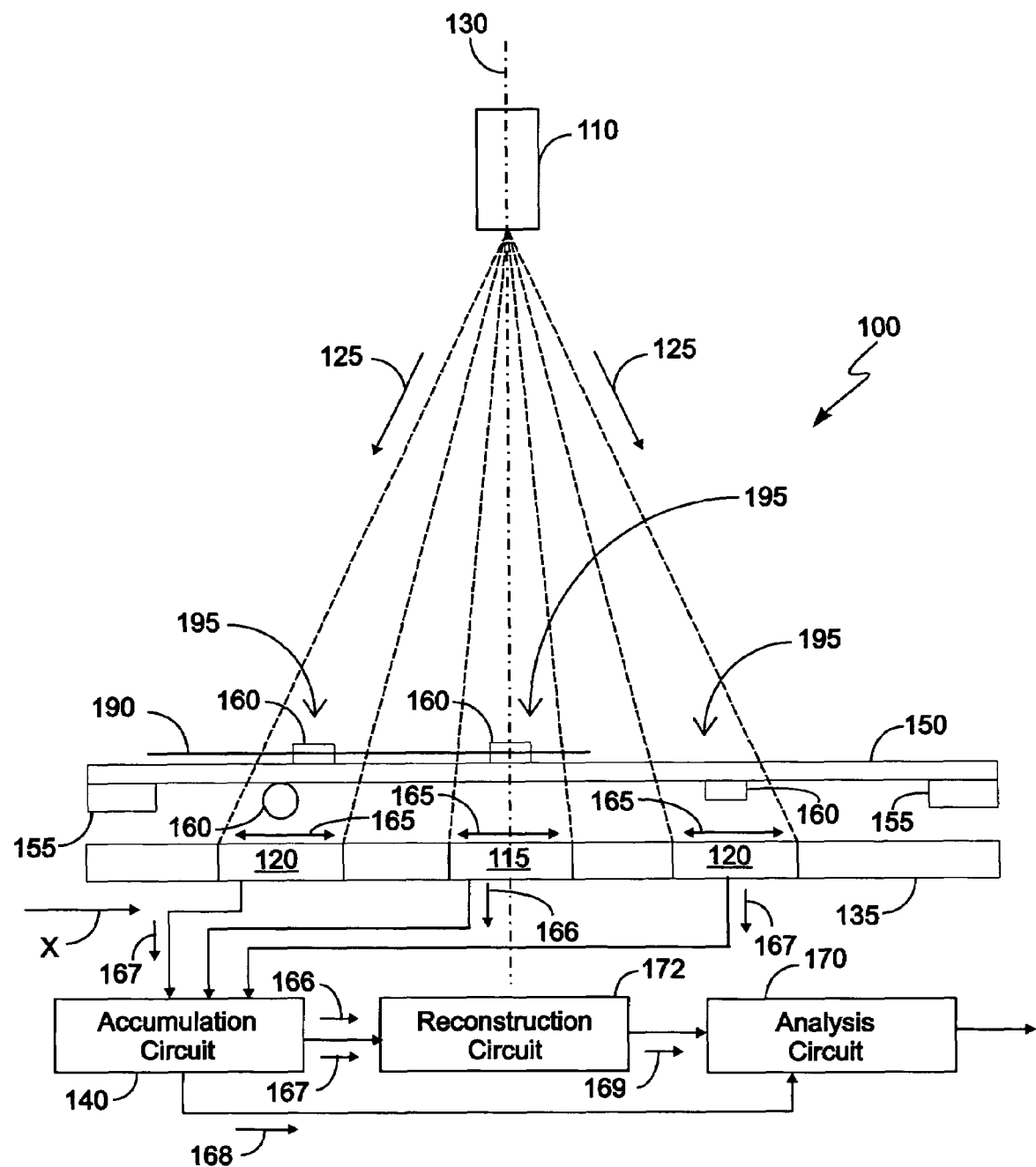
FIG. 2 is a drawing of a block diagram of the x-ray inspection system with an article placed for inspection as described in various representative embodiments.

FIG. 2 is a drawing of a block diagram of the x-ray inspection system 100 with an article 150 placed for inspection as described in various representative embodiments. FIG. 2 is similar to FIG. 1 with the inclusion of the article 150 to be inspected and a fixture 155. The fixture 155 holds the article 150 readied for inspection in a location between the x-ray source 110 and the on-axis and off-axis x-ray sensors 115,120. In the example of FIG. 2, the article 150 is printed circuit board 150 loaded with components 160. The printed circuit board 150 with its mounted components 160 or objects 160 placed between the x-ray source 110 and the x-ray sensors 115,120 cast shadows on the sensors 115,120, thereby producing images 165 captured by the x-ray sensors 115,120. What little x-ray radiation 125 that the base material of the printed circuit board 150 absorbs will be captured as a relatively uniform background shadow which will be subsequently filtered out or ignored during processing. However, radiation 125 absorbed by the components 160 will create images 165 of the components 160 captured by the sensors 115,120. The images 165 (captured by both the on-axis and off-axis x-ray sensors 115,120) are captured at any one relative position of the printed circuit board 150, the x-ray source 110, and the sensors 115, 120.

In the example of FIG. 2 are two components 160, one irradiated with x-ray radiation 125 with its corresponding image 165 being captured by the on-axis x-ray sensor 115 and one irradiated with x-ray radiation 125 with its corresponding image 165 being captured by the leftmost off-axis x-ray sensor 120 of FIG. 2, are shown on the top side of the printed circuit board 150. Also in the example of FIG. 2, the printed circuit board 150 has two other components 160 shown on the bottom side of the printed circuit board 150, one irradiated with x-ray radiation 125 with its corresponding image 165 captured by the leftmost off-axis x-ray sensor 120 and one irradiated with x-ray radiation 125 with its corresponding image 165 captured by the rightmost off-axis x-ray sensor 120. Due to component 160 overlap over the leftmost off-axis x-ray sensor 120, an image 165 is captured by that sensor 120 in which the two components 160 are not separately defined. Separation of the two components 160 is obtainable by capturing images 165 of that region 195 of the printed circuit board 150 following relative movement between the printed circuit board 150, the x-ray source 110, and the sensors 115,120 and by subsequent image processing using any of the well known tomography techniques. Relative movement between the printed circuit board 150, the x-ray source 110, and the sensors 115,120 can be obtained by any of various techniques well known in the art including rotational and linear movement. Relative linear movement may be effected in FIG. 2 by, for example, movement of the printed circuit board 150 parallel to a direction X and/or perpendicular to direction X or any other convenient direction.

The image 165 captured by the on-axis x-ray sensor 115 is referred to as the on-axis image 166, and the images 165 captured by the off-axis x-ray sensors 120 are referred to as the off-axis images 167. The images produced by both the on-axis and off-axis x-ray sensors 115, 120, i.e., the on-axis image 166 and/or the off-axis images 167, are referred to as transmission images, or alternatively as 2-D images. The transmission images 168 produced by the on-axis x-ray sensor 115 and the off-axis x-ray sensors 120 are collected by the accumulation circuit 140.

The transmission images 168 can be transferred without modification directly to an analysis circuit 170 for analysis which might be, for example, with respect to the quality of the article 150. The on-axis images 166 and off-axis images 167 can be transferred the reconstruction circuit 172 which uses mathematical processes known in the art to transform the sets of transmission images 168 (on-axis and off-axis images 166,167) into a set of reconstructed images 169, also referred to herein as layer images 169, whereby each layer image 169 is a representation of a plane section through the object space or a conceptual "layer" of the article 150 under inspection. A layer image 169 is one set of reconstructed images 169 representing the layer 190 of the article 150. Typically, this transformation consists in part of an averaging process across each of the transmission images 168 to emphasize physical characteristics of each conceptual layer 190 of the article 150. One such possible process for converting the transmission images 168 into layer images 169 is described by Adams in U.S. Pat. No. 5,583,904, entitled "Continuous Linear Scan Laminography System and Method". Alternate methods for performing essentially the same function may also be employed. In some embodiments, the transformation includes a subset of the transmission images 168. The reconstructed layer images 169, can then be transferred to the analysis circuit 170 for analysis. The reconstructed layer images 169 are also referred to as 3-D images 169.

After the layer images 169 are generated, the analysis circuit 170 may then utilize the layer images 169 to determine the overall quality of the article 150 under inspection. For example, in the case of an electronic printed circuit board 150 as shown in FIG. 2, features of each layer, such as solder joints, and the like, can be compared automatically to a preexisting set of images or structural measurements to ascertain the physical quality of the printed circuit board 150. The preexisting set of images or measurements may be generated by way of a theoretical standard or a known good printed circuit board 150. Furthermore, image processing algorithms known in the art may be employed to process key portions of the layer images to determine overall quality and other desired parameters of those portions.

Each of the off-axis x-ray sensors 120 are positioned relative to the x-ray source 110 so that the transmission image of the article 150 captured by each off-axis x-ray sensor 120 is acquired at a distinct angle relative to the x-ray source 110. While the examples of FIGS. 1 and 2 show only two off-axis x-ray sensors 120, several other off-axis x-ray sensors 120 can be arranged around the on-axis x-ray sensor 115. The off-axis x-ray sensors 120 can be conveniently placed in a circular or other configuration, resulting in a difference in viewing angle between adjacent off-axis x-ray sensors 120 of approximately 30 degrees. While any number of off-axis x-ray sensors 120 may be employed to generate different viewing angles of the article 150 under inspection, a range of twelve to sixteen off-axis x-ray sensors 120 appears to generate a sufficient number of images 165 for proper inspection of printed circuit boards. An implementation of eight off-axis x-ray sensors 120 would probably be considered a practical minimum for most inspection applications. In many cases, the use of more than sixteen off-axis x-ray sensors 120 would not add significantly to the inspection capabilities of the x-ray inspection system 100 to justify the costs involved in employing the additional sensors. The desirable number and placement of the off-axis x-ray sensors 120 are implementation dependent but not limiting upon the representative embodiments disclosed herein.

The arrangement, size, and outline of the off-axis x-ray sensors 120 is also somewhat arbitrary, as is the size and outline of the on-axis x-ray sensor 115. The off-axis x-ray sensors 120 and the on-axis x-ray sensor 115 may be circular, a square, a diamond, or a more randomized outline. Also, the off-axis x-ray sensors 120 may be arranged in a circular, a square, a diamond, a randomized or other pattern around the axis 130. Depending on the application, the configuration selection may be based to some extent on the ease of implementation of the selected configuration, and the desired image quality of the type of articles to be inspected.

Each of the on-axis and off-axis x-ray sensors 115,120 is stationary relative to each other. For representative embodiments having physically separated on-axis and off-axis x-ray sensors 115,120, this stationary condition is typically by way of attachment to a base 180 not shown in the figures. It is to be emphasized, however, that the base 180 with attached on-axis and off-axis x-ray sensors 115,120 may be either stationary or moveable relative to the article 150 and/or the x-ray source 110. In other representative embodiments, the positioning of the sensors 115,120 can be adjusted to obtain the best images for the particular application.

The on-axis and off-axis x-ray sensors 115,120, may be standard off the shelf x-ray sensors or may be specially fabricated x-ray sensors and may have a number of pixels specified by the designer of the system 100 comprising typically several hundred to a few million imaging pixels that are adapted to be sensitive to the x-rays from the x-ray source 110. The on-axis and off-axis x-ray sensors 115,120 may be, for example, commercially available 300 dot-per-inch (DPI) or 600 DPI charge-coupled device (CCD) linear sensors mounted with a fiber optic plate (FOP) and a cesium-iodide x-ray scintillator. Periodically, voltages denoting the intensity level detected by each pixel typically are transferred to a shift register that is read by the accumulation circuit 140, normally via an analog-to-digital converter (ADC). Other sensors that are sensitive to x-rays may also be employed in the x-ray inspection system 100, depending on the technical requirements of the application involved.

In alternate embodiments, either the x-ray source 110, the fixture 155, or both can move vertically relative to the plane of the on-axis and off-axis x-ray sensors 115,120. The capability of such movement provides the ability to vary the image 165 resolution of the x-ray inspection system 100. The greater the ratio of separation between the x-ray source 110 and the specified layer 190, to the separation between the x-ray source 110 and the plane 185 of the on-axis and off-axis x-ray sensors 115,120, the larger will be the region 195 of the article 150 from which an image is obtained for any given exposure. In this case, fewer images 165 will need to be captured which results in a faster imaging process. However, since the number of imaging pixels remains constant, the larger the region 195 from which the images 165 are captured the lower will be the image 165 resolution.

Figure 3:
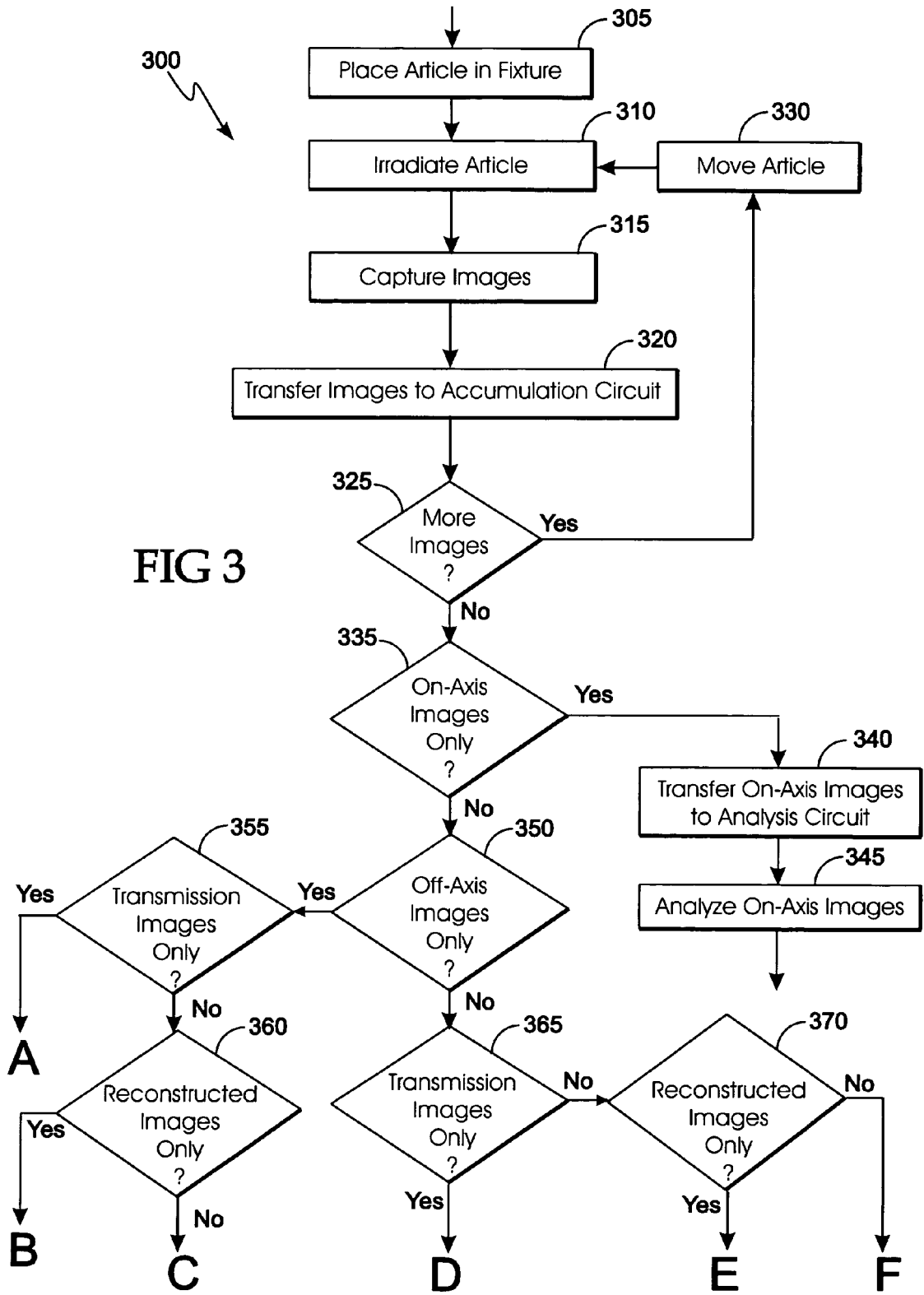
FIG. 3 is a drawing of flow chart of a method for inspecting an article using the x-ray inspection system as described in various representative embodiments.

FIG. 3 is a drawing of flow chart of a method 300 for inspecting a region 195 of an article 150 using the x-ray inspection system 100 as described in various representative embodiments. Various options are provided to the user from which can be selected the method best suited for any given application. In block 305 of FIG. 3, the article 150 is placed in fixture 155. Block 305 then transfers control to block 310.

In block 310, the article 150 is irradiated with x-ray radiation 125 from the x-ray source 110. Block 310 then transfers control to block 315.

In block 315, images 165 of the irradiated article 150 are captured by the on-axis x-ray sensor 115 and/or the off-axis x-ray sensors 120. Block 315 then transfers control to block 320.

In block 320, the captured images 165 are transferred to the accumulation circuit 140. Block 320 then transfers control to block 325.

In block 325, if there are additional images 165 to capture for region 195, block 325 transfers control to block 330. Otherwise, block 325 transfers control to block 335.

In block 330, relative movement between the article 150, the x-ray source 110, and the sensors 115,120 occurs. Block 330 then transfers control to block 310.

In block 335, if only on-axis images 166 are to be analyzed, block 335 transfers control to block 340. Otherwise, block 335 transfers control to block 350.

In block 340, the on-axis images 166 (transmission images 168) are transferred to the analysis circuit 170. Block 340 then transfers control to block 345.

In block 345, the on-axis images 166 (transmission images 168) are analyzed. Block 345 then terminates the process.

In block 350, if only off-axis images 167 are to be analyzed, block 350 transfers control to block 355. Otherwise, block 350 transfers control to block 365.

Figure 4:
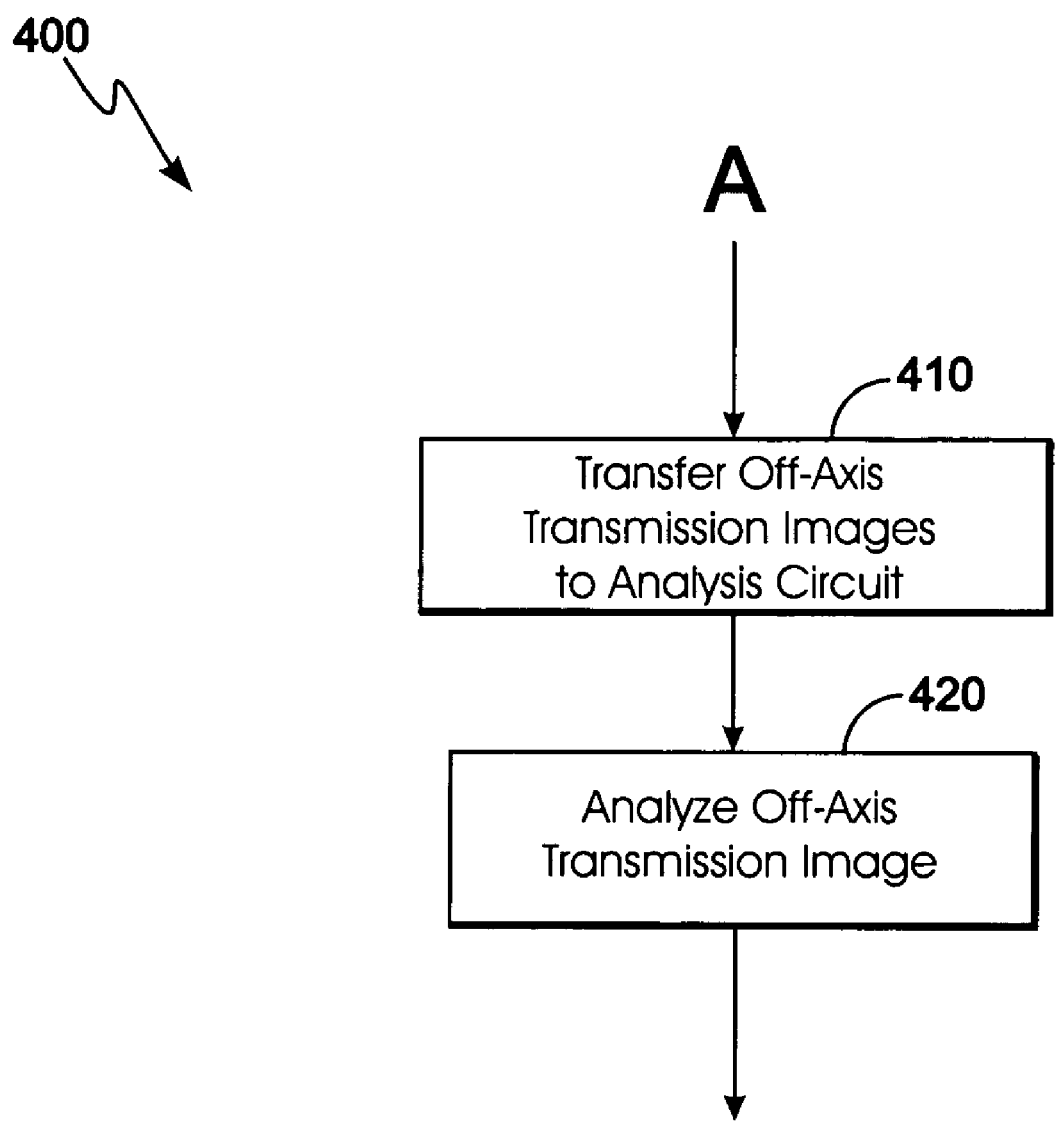
FIG. 4 is a drawing of a flow chart of a sub-method of the method of FIG. 3.

In block 355, if only transmission images 168 are to be analyzed, block 355 transfers control to block 410 at point A in the flow chart found in FIG. 4. Otherwise, block 355 transfers control to block 360.

Figure 5:
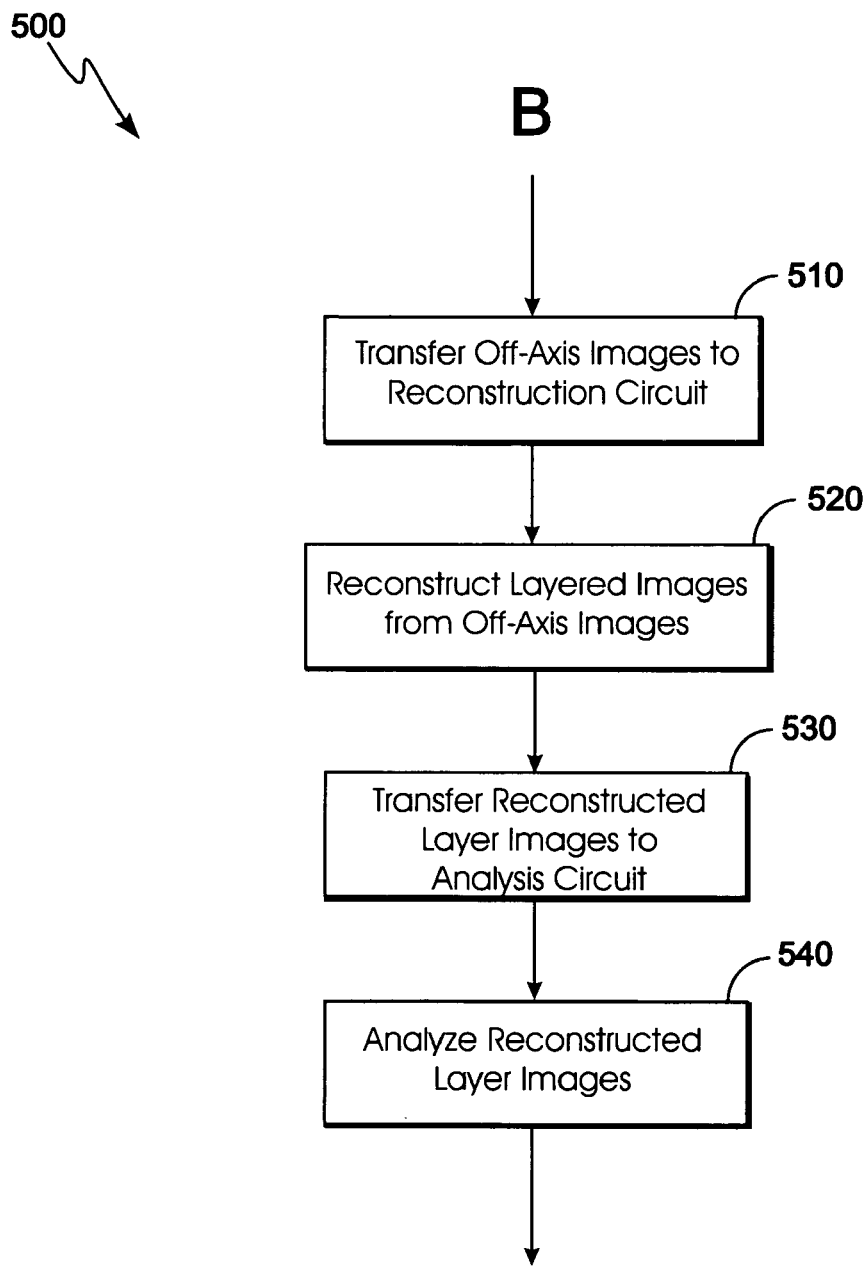
FIG. 5 is a drawing of a flow chart of another sub-method of the method of FIG. 3.

In block 360, if only reconstructed images 169 are to be analyzed, block 360 transfers control to block 510 at point B in the flow chart found in FIG. 5. Otherwise, block 360 transfers control to block 610 at point C in the flow chart found in FIG. 6.

Figure 7:
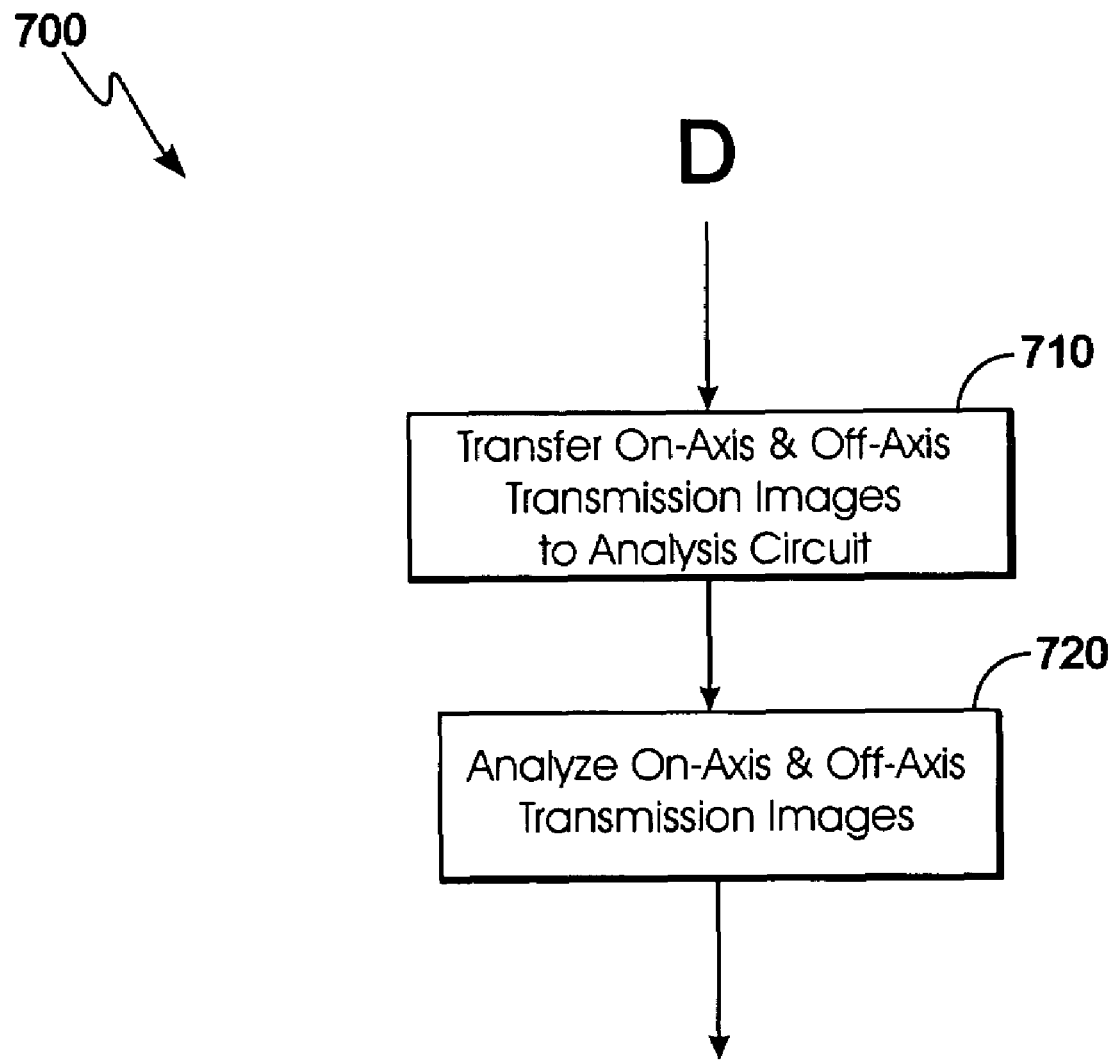
FIG. 7 is a drawing of a flow chart of yet another sub-method of the method of FIG. 3.

In block 365, if only transmission images 168 are to be analyzed, block 365 transfers control to block 710 at point D in the flow chart found in FIG. 7. Otherwise, block 365 transfers control to block 370.

Figure 8:
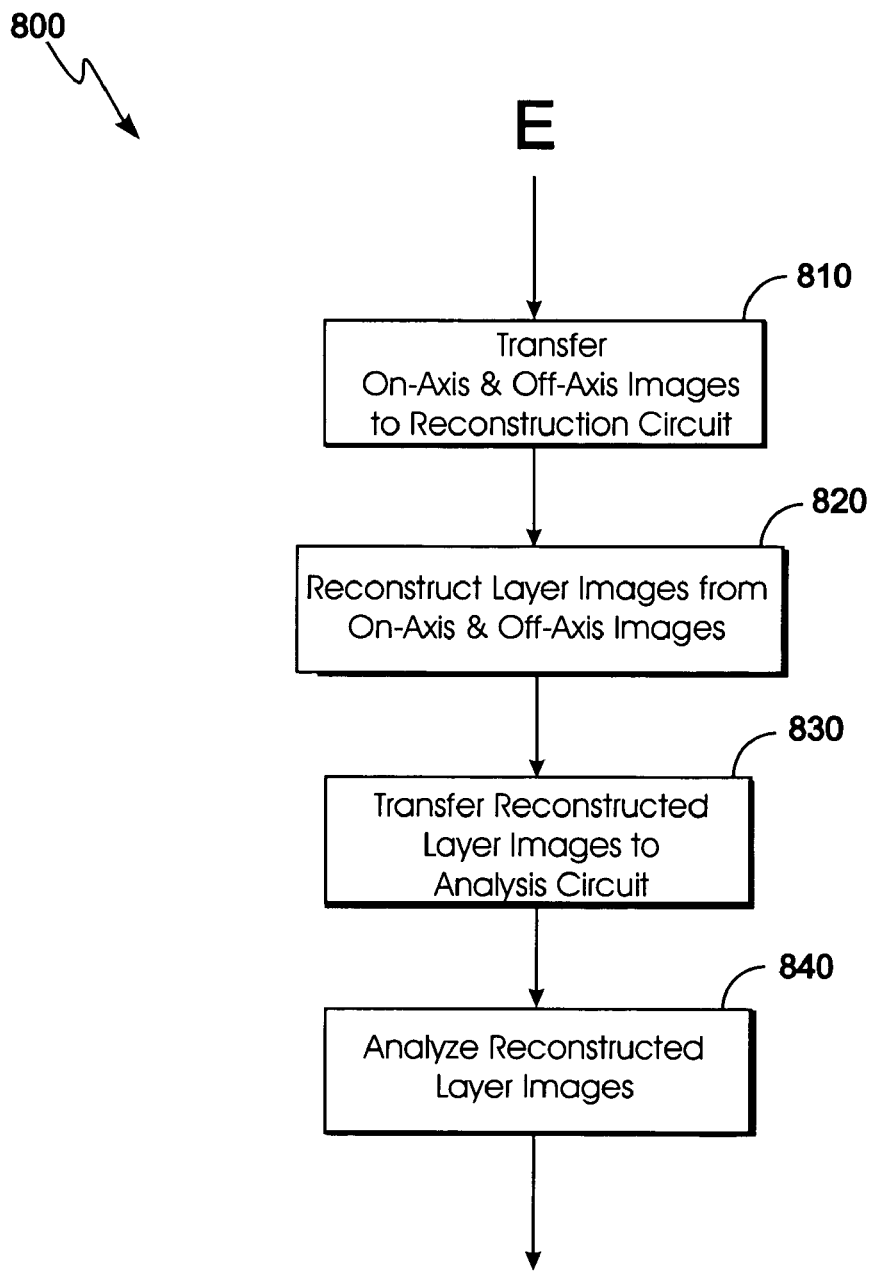
FIG. 8 is a drawing of a flow chart of an additional sub-method of the method of FIG. 3.

In block 370, if only reconstructed images 169 are to be analyzed, block 370 transfers control to block 810 at point E in the flow chart found in FIG. 8. Otherwise, block 370 transfers control to block 910 at point F in the flow chart found in FIG. 9.

FIG. 4 is a drawing of a flow chart of a sub-method 400 of the method 300 of FIG. 3. At point A in FIG. 3, block 355 conditionally transfers control to block 410 at point A in FIG. 4.

In block 410, the off-axis images 167 (transmission images 168) are transferred to the analysis circuit 170. Block 410 then transfers control to block 420.

In block 420, the off-axis images 167 (transmission images 168) are analyzed. Block 420 then terminates the process.

FIG. 5 is a drawing of a flow chart of another sub-method 400 of the method 300 of FIG. 3. At point B in FIG. 3, block 360 conditionally transfers control to block 510 at point B in FIG. 5.

In block 510, the off-axis images 167 are transferred to the reconstruction circuit 172. Block 510 then transfers control to block 520.

In block 520, reconstructed images 169 (layer images 169) are created. Each layer image 169 is a representation of a plane section through the object space or a conceptual "layer" of the article 150 under inspection. In other words, a layer image 169 is the reconstructed image 169 in a layer 190 of the article 150. Block 520 then transfers control to block 530.

In block 530, the reconstructed layer images 169 are transferred to the analysis circuit 170. Block 530 then transfers control to block 540.

In block 540, the reconstructed layer images 169 are analyzed. Block 540 then terminates the process.

Figure 6:
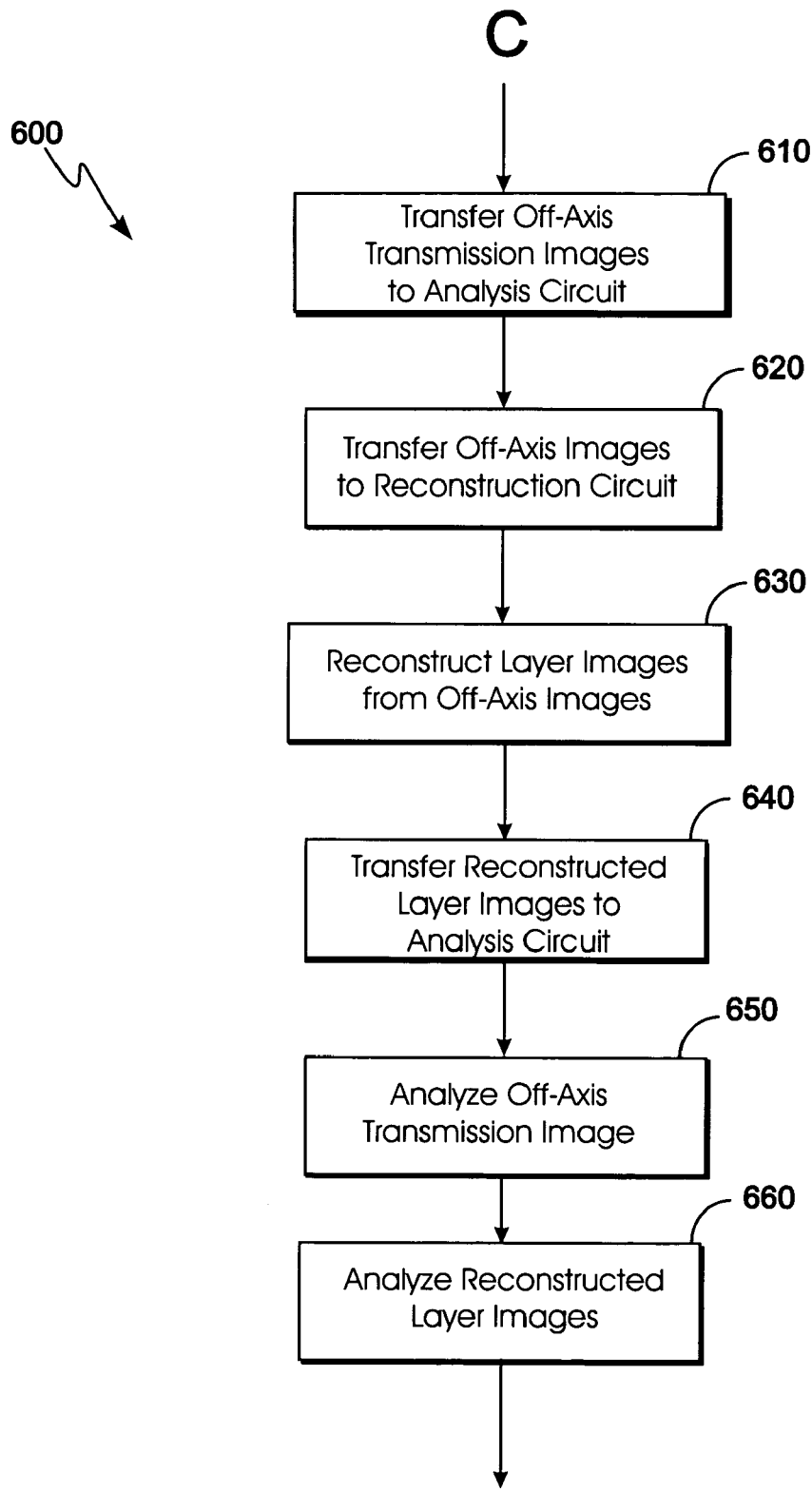
FIG. 6 is a drawing of a flow chart of still another sub-method of the method of FIG. 3.

FIG. 6 is a drawing of a flow chart of still another sub-method 400 of the method 300 of FIG. 3. At point C in FIG. 3, block 360 conditionally transfers control to block 610 at point C in FIG. 6.

In block 610, the off-axis images 167 (transmission images 168) are transferred to the analysis circuit 170. Block 610 then transfers control to block 620.

In block 620, the off-axis images 167 are transferred to the reconstruction circuit 172. Block 620 then transfers control to block 630.

In block 630, reconstructed images 169 (layer images 169) are created. Block 630 then transfers control to block 640.

In block 640, the reconstructed layer images 169 are transferred to the analysis circuit 170. Block 640 then transfers control to block 650.

In block 650, the off-axis images 167 (transmission images 168) are analyzed. Block 650 then transfers control to block 660.

In block 660, the reconstructed images 169 are analyzed. Block 660 then terminates the process.

FIG. 7 is a drawing of a flow chart of yet another sub-method 400 of the method 300 of FIG. 3. At point D in FIG. 3, block 365 conditionally transfers control to block 710 at point D in FIG. 7.

In block 710, the on-axis and off-axis images 166,167 (transmission images 168) are transferred to the analysis circuit 170. Block 710 then transfers control to block 720.

In block 720, the on-axis and off-axis images 166,167 (transmission images 168) are analyzed. Block 720 then terminates the process.

FIG. 8 is a drawing of a flow chart of an additional sub-method 400 of the method 300 of FIG. 3. At point E in FIG. 3, block 370 conditionally transfers control to block 810 at point E in FIG. 8.

In block 810, the on-axis and off-axis images 166,167 are transferred to the reconstruction circuit 172. Block 810 then transfers control to block 820.

In block 820, reconstructed images 169 (layer images 169) are created from the on-axis and off-axis images 166,167. Block 820 then transfers control to block 830.

In block 830, the reconstructed layer images 169 are transferred to the analysis circuit 170. Block 830 then transfers control to block 840.

In block 840, the reconstructed layer images 169 are analyzed. Block 840 then terminates the process.

Figure 9:
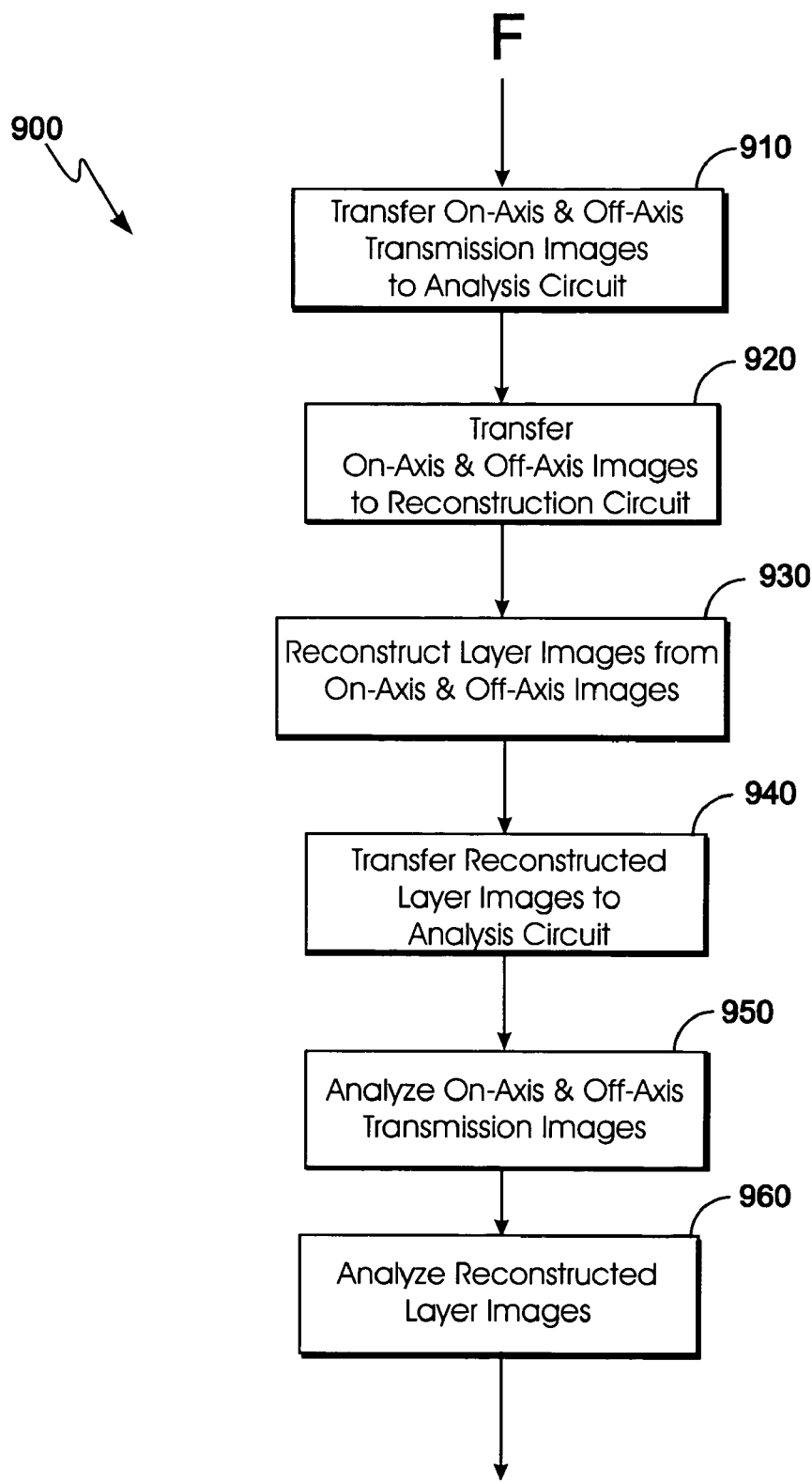
FIG. 9 is a drawing of a flow chart of still an additional sub-method of the method of FIG. 3.

FIG. 9 is a drawing of a flow chart of still an additional sub-method 400 of the method 300 of FIG. 3. At point F in FIG. 3, block 370 conditionally transfers control to block 910 at point F in FIG. 9.

In block 910, the on-axis and off-axis images 166,167 (transmission images 168) are transferred to the analysis circuit 170. Block 910 then transfers control to block 920.

In block 920, the on-axis and off-axis images 166,167 are transferred to the reconstruction circuit 172. Block 920 then transfers control to block 930.

In block 930, reconstructed images 169 (layer images 169) are created from the on-axis and off-axis images 166,167. Block 930 then transfers control to block 940.

In block 940, the reconstructed layer images 169 are transferred to the analysis circuit 170. Block 940 then transfers control to block 950.

In block 950, the on-axis and off-axis images 166,167 (transmission images 168) are analyzed. Block 950 then transfers control to block 960.

In block 960, the reconstructed layer images 169 are analyzed. Block 960 then terminates the process.

Figure 10A:
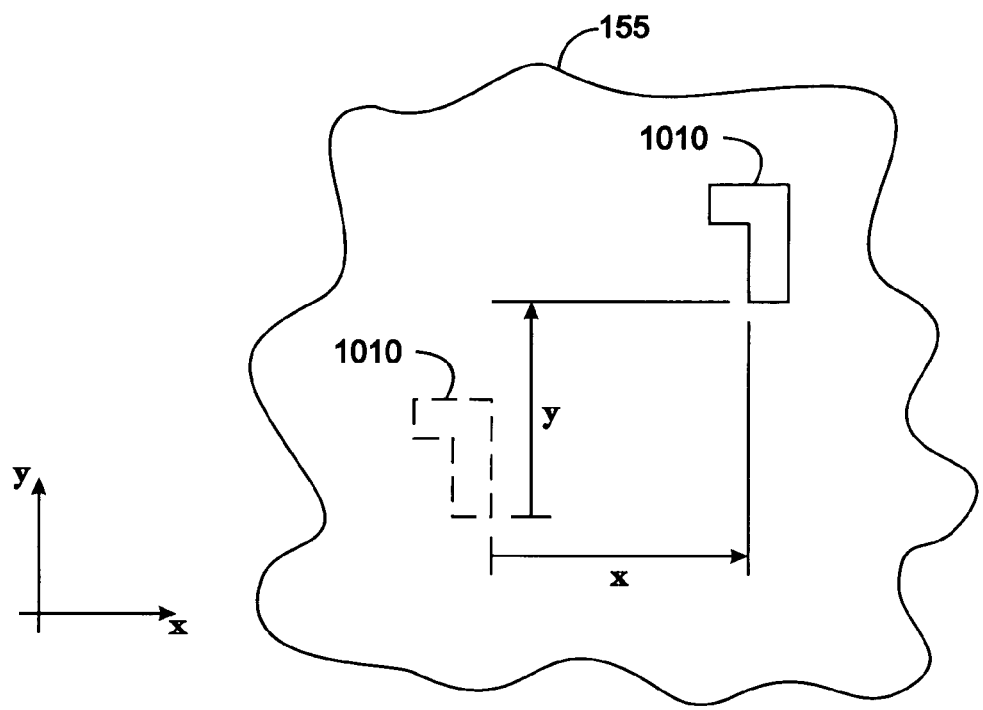
FIG. 10A is a drawing of a pattern on the fixture as described in various representative embodiments.

FIG. 10A is a drawing of a pattern 1010 on the fixture 155 as described in various representative embodiments. In alternative embodiments, the pattern 1010 can be on the article 150. In FIG. 10A the fixture 155 that comprises a known pattern 1010 or feature 1010, which could be for example an alignment mark 1010 or a fiducial mark 1010, is moved from a first to a second position. In the first position, the feature 1010 is shown dashed and after movement of a distance x in the X direction and a distance y in the Y direction to the second position by a solid outline.

Positional calibrations can be performed by placing a known feature 1010, such as a fiducial mark 1010, in an object plane. A shadow of the feature 1010 due to x-ray irradiation is projected onto the image plane. The resultant image 165 captured by the off-axis x-ray sensor 120 will experience an x-y shift as a result of a vertical height of in an object. When the feature 1010 is positioned on the axis 130, its image 165 captured by the on-axis x-ray sensor 115 will not experience an x-y shift as a result of the vertical height of the object. Therefore, the system using the on-axis x-ray sensor 115 which is positioned directly below the x-ray source 110 can determine the X-Y direction and/or magnitude of relative movement of the fixture 155 and article 150 independent of any height in the Z direction. To determine the magnitude of movement, other parameters of the system, including the magnification of the feature 1010 and the distance between the x-ray source 110 and the x-ray sensors 115,120, must also be known. Multiple features 1010 can also be imaged and measured in determining the direction and magnitude of motion.

Figure 10B:
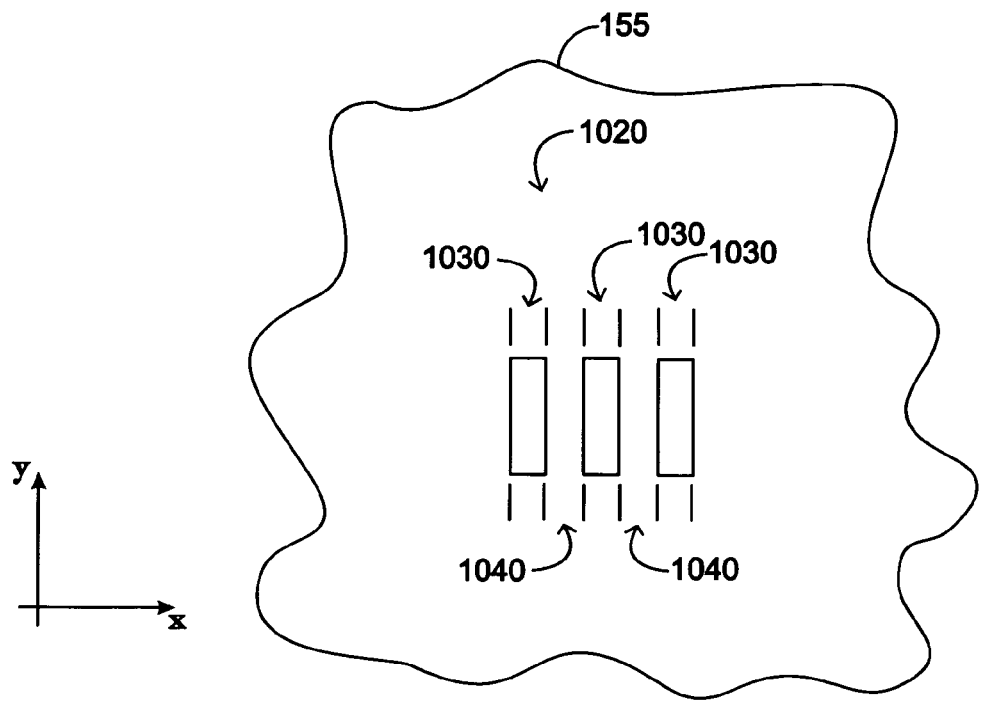
FIG. 10B is a drawing of another pattern on the fixture as described in various representative embodiments.

FIG. 10B is a drawing of another pattern 1020 on the fixture 155 as described in various representative embodiments. In alternative embodiments, the other pattern 1020 can be on the article 150. This other feature 1020 can be a set of lines 1020 of a known nominal line width 1030 which are separated by a known nominal space width 1040. This set of lines 1020 can be used to measure the resolution of the x-ray inspection system 100. While only one set of lines 1020 is shown in FIG. 10B, multiple sets of lines 1020 can be used. Measured line widths 1030 and/or measured space widths 1040 of various sets of lines 1020 provide a measurement of the resolution of the system. Other techniques, for example moving an x-ray spot across the edge of a feature and observing the signal received from the on-axis sensor 115 which could include when the signal reaches a predetermined relative signal strength, can also be used to measure resolution. Resolution measurements are commonly made by imaging a thin sharp edge by techniques known to those skilled in the art. However, it is difficult to manufacture thin features that will have attenuation large enough to produce high contrast images 165. In practice, then the edge is thick. The shadow of the top edge of this thick feature and the bottom of this thick feature will not coincide in the image 165 captured by the off-axis x-ray sensors 120. If the thick edge is positioned on the axis 130 the shadow of the top edge and the bottom edge will coincide in the image 165 captured by the on-axis x-ray sensor 115. When the shadow of the top and bottom edges do not coincide, error is introduced into the resolution measurement.

The on-axis x-ray sensor 115 is nearer to the x-ray source 110, than the off-axis x-ray sensors 120, which results in an x-ray radiation 125 intensity that is higher for the on-axis x-ray sensor 115 than for the off-axis x-ray sensor 120. The result is that the on-axis x-ray sensor 115 has a better in signal to noise ratio (Poisson Noise) than the off-axis x-ray sensors 120 do. Thus, the repeatability of the measurement will be better for the on-axis x-ray sensor 115 than for the off-axis x-ray sensor 120.

Features of representative embodiments disclosed herein include an on-axis x-ray sensor 115 and a least one off-axis x-ray sensor 120. The on-axis x-ray sensor 115 is located directly below the x-ray source 110. The image 165 from the on-axis x-ray sensor 115 is captured simultaneously with the images 165 from the off-axis x-ray sensors 120. This x-ray inspection system 100 can be used in a number of ways as follows: (a) to obtain and analyze 2-D images (transmission images) using only the on-axis image 166, (b) to obtain and analyze 2-D images (transmission images) using only the off-axis images 167, (c) to obtain and analyze 3-D images (reconstructed images) using only the off-axis images 167, (d) to obtain and analyze 2-D images (transmission images) and 3-D images (reconstructed images) using only the off-axis images 167, (e) to obtain and analyze 2-D images (transmission images) using the on-axis and off-axis images 166,167, (f) to obtain and analyze 3-D images (reconstructed images) using the on-axis and off-axis images 166,167, and (g) to obtain and analyze 2-D images (transmission images) and 3-D images (reconstructed images) using the on-axis and off-axis images 166,167.

In various applications, only sub-sets of the on-axis and off-axis images 166,167 will be needed to efficiently obtain various transmission and/or reconstructed images for analysis. In some applications, wherein one device on the article 150 is covered by another device, it may be necessary to obtain reconstructed layer images 169 whereas in other applications, one or more transmission images 168 may suffice. The on-axis image 166 can be combined with the off-axis images 167 to obtain improved tomograhic reconstruction. The on-axis image 165 can be combined with the other off-axis images 165 to provide additional information for the reconstructed layer images 169. Note that images for both reconstruction and transmission can be captured simultaneously. Further, a more accurate positional calibration of the article 150 with respect to the x-ray source 110 and x-ray sensors 115,120 can be obtained in representative embodiments disclosed herein.

Just as the on-axis image 166 can be used as a transmission image 168 and to assist in creating a reconstructed image 169, other images (the off-axis images 167) can do the same. In fact, a "transmission" image can be obtained, from any angle, as long as there is a sensor to capture the image. While the image of the feature will be projected onto the surface at the angle, it nevertheless contains information. Furthermore, any combination of images could be used to reconstruct an image. For example, if one off-axis image 167, was completely obscured (i.e. contained no desirable information), it can be left out of the reconstruction. Thus, images 165 can be selectively discarded from those to be used in the reconstruction.

During testing of a printed circuit board 150, if a solder joint's shadow is not obstructed by another feature, then the on-axis image 166 can be used in transmission mode, and if a joint's shadow is obstructed, then reconstructed images 169 are typically used. Transmission images 168 can be used even if a joint is obstructed as long as the obstruction is relatively constant. This is because thickness calibration can be used to compensate for the obstruction. Also, in some cases, the on-axis image 166 of a particular device may be obstructed, but the off-axis image 167 of that same device, taken at another time, may not be obstructed.

Note that the on-axis image 166 may have a lower signal-to-noise ratio than the reconstructed image 169. The reconstruction image's 169 noise will be lower because several images are combined. However this effect is somewhat mitigated, because the on-axis image 166 is closer to the x-ray source 110 and thus its noise will be less than any single off-axis image 167.

It will be recognized by one of ordinary skill in the art that, while in the representative embodiments disclosed above the on-axis and off-axis images 166,167 are gathered simultaneously, albeit for different regions 195, other embodiments may capture the on-axis and off-axis images 166,167 at different times.

As is the case, in many data-processing products, the systems described above may be implemented as a combination of hardware and software components. Moreover, the functionality required for use of the representative embodiments may be embodied in computer-readable media (such as floppy disks, conventional hard disks, DVDs, CD-ROMs, Flash ROMs, nonvolatile ROM, and RAM) to be used in programming an information-processing apparatus (e.g., a computer) to perform in accordance with the techniques so described.

The term "program storage medium" is broadly defined herein to include any kind of computer memory such as, but not limited to, floppy disks, conventional hard disks, DVDs, CD-ROMs, Flash ROMs, nonvolatile ROM, and RAM.

The transmission and reconstructed images can be displayed on a computer monitor which may be monochrome or color.

The representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. An x-ray inspection system, comprising:
    an x-ray source;
    an on-axis x-ray sensor configured to capture on-axis images of radiation from the x-ray source, wherein the x-ray source is displaced from the on-axis x-ray sensor, wherein the x-ray source and the on-axis x-ray sensor are positioned on an axis conceptually drawn between the x-ray source and the on-axis x-ray sensor, and wherein a sensing surface of the on-axis x-ray sensor is located in a plane whose normal is substantially parallel to the axis;
    at least one off-axis x-ray sensor configured to capture off-axis images of radiation from the x-ray source, wherein each of the at least one off-axis x-ray sensor is positioned off the axis;
    a fixture configured to maintain an article between i) the x-ray source, and ii) the on-axis x-ray sensor and the at least one off-axis x-ray sensor, wherein the fixture is movable with respect to the x-ray source, the on-axis x-ray sensor, and the at least one off-axis x-ray sensor;
    an accumulation circuit configured to receive and accumulate images captured by the on-axis x-ray sensor and the at least one off-axis x-ray sensor; and
    an analysis circuit configured to i) receive on-axis images from the accumulation circuit, ii) identify a feature of the article or the fixture, which feature is captured in at least one of the on-axis images, and iii) determine, at least in part from the identified feature, positional calibration information for the x-ray inspection system.

2. The x-ray inspection system as recited in claim 1, wherein the positional calibration information comprises a direction of relative movement of the fixture or the article with respect to the x-ray source, the on-axis x-ray sensor, and the at least one off-axis x-ray sensor.

3. The x-ray inspection system as recited in claim 1, wherein the positional calibration information comprises a magnitude of relative movement of the fixture or the article with respect to the x-ray source, the on-axis x-ray sensor, and the at least one off-axis x-ray sensor.

4. An x-ray inspection system, comprising:
    an x-ray source;
    an on-axis x-ray sensor configured to capture on-axis images of radiation from the x-ray source, wherein the x-ray source is displaced from the on-axis x-ray sensor, wherein the x-ray source and the on-axis x-ray sensor are positioned on an axis conceptually drawn between the x-ray source and the on-axis x-ray sensor, and wherein a sensing surface of the on-axis x-ray sensor is located in a plane whose normal is substantially parallel to the axis;
    at least one off-axis x-ray sensor configured to capture off-axis images of radiation from the x-ray source, wherein each of the at least one off-axis x-ray sensor is positioned off the axis;
    a fixture configured to maintain an article between i) the x-ray source, and ii) the on-axis x-ray sensor and the at least one off-axis x-ray sensor, wherein the fixture is movable with respect to the x-ray source, the on-axis x-ray sensor, and the at least one off-axis x-ray sensor;
    an accumulation circuit configured to receive and accumulate images captured by the on-axis x-ray sensor and the at least one off-axis x-ray sensor; and
    an analysis circuit configured to i) receive at least one on-axis image from the accumulation circuit, ii) identify a feature of the article or the fixture, which feature is captured in at least one of the at least one on-axis image received from the accumulation circuit, and iii) determine, at least in part from the identified feature, a resolution of the x-ray inspection system.

5. The x-ray inspection system as recited in claim 4, wherein the feature is a set of lines having known line widths, and wherein determining the resolution of the x-ray inspection system comprises measuring the line widths.

6. The x-ray inspection system as recited in claim 4, wherein the feature is a set of lines separated by a set of spaces having known space widths, and wherein determining the resolution of the x-ray inspection system comprises measuring the space widths.

7. An x-ray inspection system, comprising:
    an x-ray source;
    an on-axis x-ray sensor configured to capture on-axis images of radiation from the x-ray source, wherein the x-ray source is displaced from the on-axis x-ray sensor, wherein the x-ray source and the on-axis x-ray sensor are positioned on an axis conceptually drawn between the x-ray source and the on-axis x-ray sensor, and wherein a sensing surface of the on-axis x-ray sensor is located in a plane whose normal is substantially parallel to the axis;
    a plurality of off-axis x-ray sensors configured to capture off-axis images of radiation from the x-ray source, wherein each of the plurality of off-axis x-ray sensors is positioned off the axis;

a fixture configured to maintain an article between i) the x-ray source, and ii) the on-axis x-ray sensor and the plurality of off-axis x-ray sensors, wherein the fixture is movable with respect to the x-ray source, the on-axis x-ray sensor, and the plurality of off-axis x-ray sensors;

an accumulation circuit configured to i) receive and accumulate transmission images captured by the on-axis x-ray sensor and the plurality of off-axis x-ray sensors, and ii) capture at least some of the transmission images at different locations of the article with respect to the x-ray source, the on-axis x-ray sensor, and the plurality of off-axis x-ray sensors;

a reconstruction circuit configured to i) receive at least some of the transmission images captured at the different locations, and ii) reconstruct at least one layer image from the transmission images, wherein the at least one layer image provides at least one view of the article in at least one specified layer; and an analysis circuit configured to determine parameters of a plurality of features of the article by i) using one or more of the layer images to determine a parameter of at least a first one of the plurality of features, and ii) using one or more of the transmission images to determine a parameter of at least a second one of the plurality of features.

8. The x-ray inspection system as recited in claim 7, wherein the reconstruction circuit is configured to reconstruct the at least one layer image from one or more of i) the transmission images captured by the on-axis x-ray sensor, and ii) a number of the transmission images captured by one or more of the plurality of off-axis x-ray sensors.

9. The x-ray inspection system as recited in claim 7, wherein the one or more transmission images used by the analysis circuit comprise i) the transmission images captured by the on-axis x-ray sensor, and ii) a number of the transmission images captured by one or more of the plurality of off-axis x-ray sensors.

10. The x-ray inspection system as recited in claim 7, wherein the accumulation circuit is configured to selectively discard certain ones of the transmission images.

11. A method for inspecting an article by the use of x-rays, comprising:

placing an article on a fixture configured to maintain the article between i) an x-ray source, and ii) an on-axis x-ray sensor positioned to receive on-axis radiation emitted by the x-ray source, and a plurality of off-axis x-ray sensors positioned to receive off-axis radiation emitted by the x-ray source;

irradiating the article with radiation emitted by the x-ray source;

capturing transmission images of the irradiated article using both the on-axis x-ray sensor and the plurality of off-axis x-ray sensors;

using at least some of the transmission images to reconstruct at least one layer image that provides at least one view of the article in at least one specified layer; and determining parameters of a plurality of features of the article by i) using one or more of the at least one layer image to determine a parameter of at least a first one of the plurality of features, and ii) using one or more of the transmission images to determine a parameter of at least a second one of the plurality of features, and displaying and/or storing the parameters.

12. The method of claim 11, wherein only transmission images captured by the plurality of off-axis x-ray sensors are used to reconstruct at least one of the at least one layer image.

13. The method of claim 11, wherein transmission images captured by at least some of the plurality of off-axis x-ray sensors, and transmission images captured by the on-axis x-ray sensor, are used to reconstruct at least one of the at least one layer image.

14. A method for inspecting an article by the use of x-rays, comprising:

using an x-ray source to irradiate a feature in an object plane, the object plane being positioned between i) the x-ray source, and ii) an on-axis x-ray sensor positioned to receive on-axis radiation emitted by the x-ray source, and a plurality of off-axis x-ray sensors positioned to receive off-axis radiation emitted by the x-ray source;

capturing a transmission image of the feature using the on-axis x-ray sensor;

determining, at least in part from the transmission image of the feature, positional calibration information for an x-ray inspection system in which the x-ray source, the on-axis x-ray sensor, and the plurality of off-axis x-ray sensors are mounted;

placing an article on a fixture configured to maintain the article between i) the x-ray source, and ii) the on-axis x-ray sensor and the plurality of off-axis x-ray sensors;

irradiating the article with radiation emitted by the x-ray source;

capturing transmission images of the irradiated article using at least some of the plurality of off-axis x-ray sensors;

using at least some of the transmission images of the irradiated article to reconstruct at least one layer image that provides at least one view of the article in at least one specified layer; and using one or more of the at least one layer image to determine a parameter of a feature of the article, and displaying and/or storing the parameters.

15. The method of claim 14, wherein the positional calibration information comprises a direction of relative movement of the feature in the object plane with respect to the x-ray source, the on-axis x-ray sensor, and the plurality of off-axis x-ray sensors.

16. The method of claim 14, wherein the positional calibration information comprises a magnitude of relative movement of the feature in the object plane with respect to the x-ray source, the on-axis x-ray sensor, and the plurality of off-axis x-ray sensors.

17. A method for inspecting an article by the use of x-rays, comprising:

using an x-ray source to irradiate a feature in an object plane, the object plane being positioned between i) the x-ray source, and ii) an on-axis x-ray sensor positioned to receive on-axis radiation emitted by the x-ray source, and a plurality of off-axis x-ray sensors positioned to receive off-axis radiation emitted by the x-ray source;

capturing a transmission image of the feature using the on-axis x-ray sensor;

determining, at least in part from the transmission image of the feature, a resolution of an x-ray inspection system in which the x-ray source, the on-axis x-ray sensor, and the plurality of off-axis x-ray sensors are mounted;

placing an article on a fixture configured to maintain the article between i) the x-ray source, and ii) the on-axis x-ray sensor and the plurality of off-axis x-ray sensors;

irradiating the article with radiation emitted by the x-ray source;

capturing transmission images of the irradiated article using at least some of the plurality of off-axis x-ray sensors;

using at least some of the transmission images of the irradiated article to reconstruct at least one layer image that provides at least one view of the article in at least one specified layer; and using one or more of the at least one layer image to determine a parameter of a feature of the article, and displaying and/or storing the parameters.

18. The method of claim 17, wherein the feature in the object plane is a set of lines having known line widths, and wherein determining the resolution of the x-ray inspection system comprises measuring the line widths.

19. The method of claim 17, wherein the feature is a set of lines separated by a set of spaces having known space widths, and wherein determining the resolution of the x-ray inspection system comprises measuring the space widths.

* * * * *